United States Patent [19]

Sabol et al.

[11] 4,104,291

[45] Aug. 1, 1978

[54] METAL DITHIOPHOSPHATES AND THEIR MANUFACTURE

[75] Inventors: Albert R. Sabol, Munster, Ind.; Nicholas C. Petrellis, Lisle, Ill.

[73] Assignee: Standard Oil Company a corporation of Indiana, Chicago, Ill.

[21] Appl. No.: 781,626

[22] Filed: Mar. 28, 1977

[51] Int. Cl.$^2$ .............................................. C07F 3/06
[52] U.S. Cl. ........................... 260/429.9; 252/32.7 E; 260/429 R; 260/439 R; 260/987
[58] Field of Search ............... 260/429.9, 987, 429 R, 260/439 R; 252/32.7 E

[56] References Cited

U.S. PATENT DOCUMENTS

| | | | |
|---|---|---|---|
| 3,014,940 | 12/1961 | Lynch et al. | 260/429.9 X |
| 3,086,939 | 4/1963 | Tichelaar | 260/429.9 X |
| 3,234,250 | 2/1966 | Schneider et al. | 260/429.9 |
| 3,290,347 | 12/1966 | Miller | 260/429.9 |
| 3,293,181 | 12/1966 | Stuart | 260/429.9 X |
| 3,428,662 | 2/1969 | Millendorf et al. | 260/429.9 |
| 3,442,804 | 5/1969 | LeSuer et al. | 260/429.9 X |
| 3,515,712 | 6/1970 | Goldsmith | 260/429.9 X |
| 3,562,306 | 2/1971 | Blaha et al. | 260/429.9 |
| 3,686,243 | 8/1972 | Rigdon et al. | 260/429.9 |

OTHER PUBLICATIONS

Perry, Chemical Engineer's Handbook, McGraw-Hill Book Co., N.Y., 4th Ed., pp. 21-23 to 21-25 (1963).

*Primary Examiner*—Helen M. S. Sneed
*Attorney, Agent, or Firm*—Frank J. Sroka; Arthur G. Gilkes; William T. McClain

[57] ABSTRACT

Disclosed are a process for the manufacture of metal dithiophosphates especially the neutralization of dithiophosphoric acids, and also the product made by such process. The process for the continuous neutralization of dithiophosphoric acid with metal base comprises contacting dithiophosphoric acid with metal base to form a neutralization mixture; passing said neutralization mixture through a static mixer in order to achieve mixing of the neutralization mixture and substantial neutralization of said dithiophosphoric acid; cooling the substantially neutralized dithiophosphoric acid; and recovering metal dithiophosphate.

13 Claims, 1 Drawing Figure

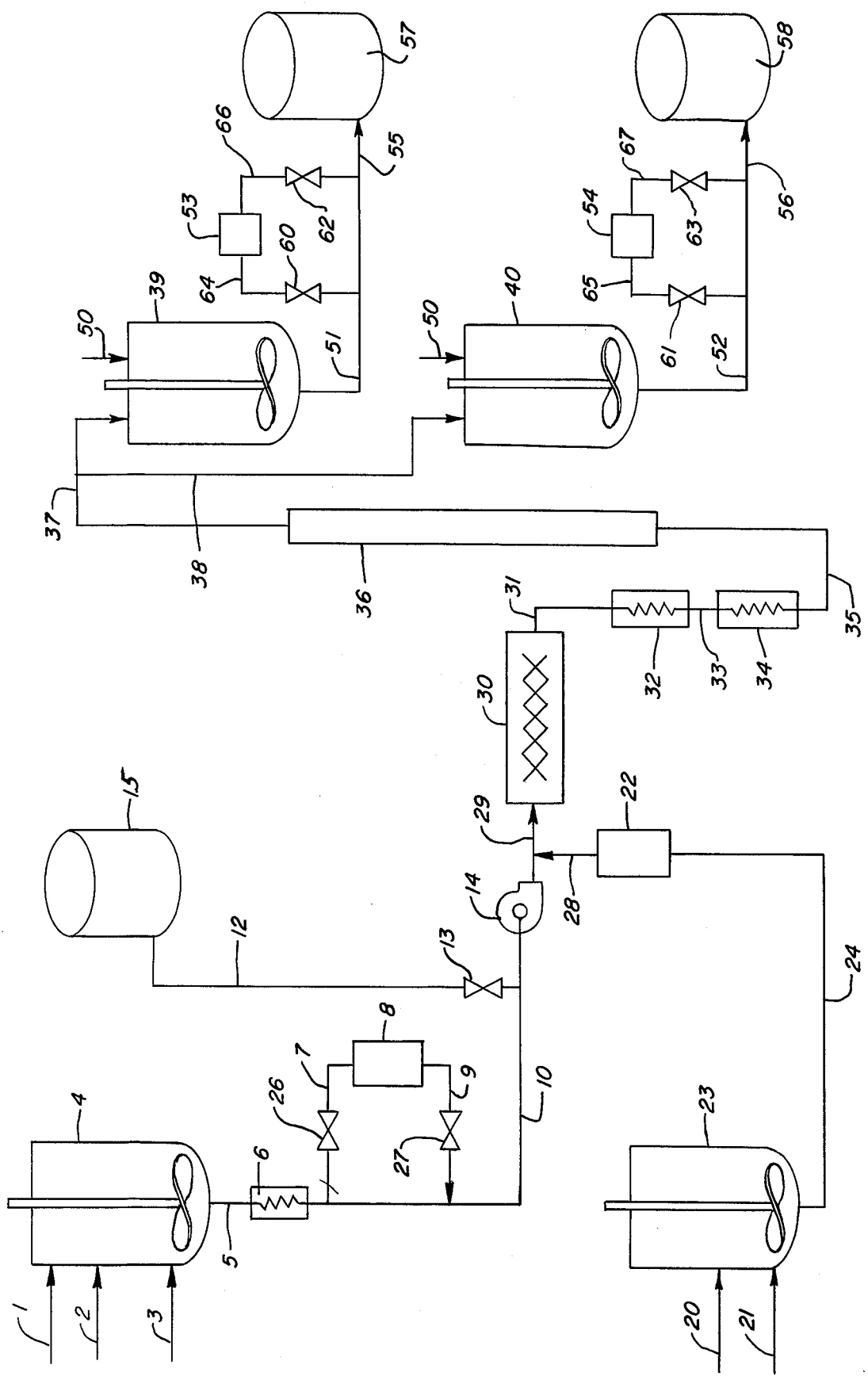

METAL DITHIOPHOSPHATES AND THEIR MANUFACTURE

BACKGROUND

This invention relates to the manufacture of metal dithiophosphates and to the composition manufactured. More specifically this invention relates to a process for the neutralization of dithiophosphoric acids.

It is well known that various additives can be added to lubricating oils in order to improve various oil properties and to make a more satisfactory lubricant. Antiwear agents are intended to decrease wear of machine parts. Wear inhibitors for incorporation in motor oils and industrial oils are finding greater use as a result of greater stress placed on moving parts in high performance engines. Numerous additives have been developed for use in such oil compositions to improve the lubricating characteristics thereof and thereby to lessen the wear of the moving parts.

Metal diaryl or dialkyl dithiophosphates, especially zinc diaryl or dialkyl dithiophosphates (ZOP), have long been used as antiwear additives and antioxidants in hydraulic oils, motor oils and automatic transmission fluids. In the manufacture of such metal dithiophosphates, a dithiophosphoric acid is commonly neutralized with a base, such as zinc oxide or hydroxide. This neutralization step does not take place readily and commonly a large excess of the base is used in conjunction with a neutralization promoter and high neutralization temperatures in order to achieve reasonably short reaction time. Sometimes the use of promoters such as nitric acid can lead to undesirable side effects such as haze problems or instability. In many cases the neutralized product is difficult to filter and has a dark color.

It is an object of this invention to provide an improved process for the manufacture of metal dithiophosphates, especially neutralization of dithiophosphoric acids.

It is an object of this invention to provide an improved process for the continuous neutralization of dithiophosphoric acids requiring shorter neutralization time, a minimum amount of excess metal base, and often requiring no neutralization promoter. Further, this process has a high throughput at minimum capital expenditure. In many cases, highly effective dithiophosphates are made which do not suffer possible detrimental affects of neutralization promoters.

SUMMARY OF THE INVENTION

Disclosed are a process for the manufacture of metal dithiophosphates, especially the neutralization of dithiophosphoric acids, and also the product made by such process.

Metal dithiophosphates are generally made by the reaction alcohol with $P_2S_5$ to form dithiophosphoric acid or phosphoric acid ester. Most commonly the alcohols are alkyl, aryl or alkaryl. In some cases the $P_2S_5$ is reacted with a second compound in addition to alcohol. However, dialkyl and diaryl dithiophosphoric acids are preferred. In any event, the dithiophosphoric acid is then neutralized with metal base, especially zinc, barium, cadmium, magnesium or nickel base. Zinc oxide is the preferred base because of its low cost and because of the commercial significance of ZOP in the lubricating oil field.

The process for the continuous neutralization of dithiophosphoric acid with metal base comprises contacting dithiophosphoric acid with metal base to form a neutralization mixture; passing said neutralization mixture through a static mixer in order to achieve mixing of the neutralization mixture and substantial neutralization of said dithiophosphoric acid; cooling the substantially neutralized dithiophosphoric acid; and recovering metal dithiophosphate.

Static mixers are mixing devices that generally have no mixing parts. They generally comprise pipes containing stationary baffle arrangements on the inside. Fluids passing through these devices use the energy of the flowing fluid to produce mixing. Static mixers are available commercially, and Koch mixers are considered quite suitable.

Preferably, after the neutralization mixture passes through the static mixer, the mixture is passed through a vessel in order to increase the contact time between the base and the dithiophosphoric acid in the mixture. In this manner, essentially complete neutralization is effected. It is also preferred to blow the neutralization mixture with inert gas such as nitrogen in order to remove water of neutralization after mixture has been essentially completely neutralized.

In the neutralization reaction, about 0.5 to about 1.0 moles, preferably about 0.6 to about 0.8 moles, of metal base per mole of dithiophosphoric acid is used. The neutralization is generally conducted at a temperature of about 100° to about 210° F, but preferably about 100° to about 170° F.

Generally, this continuous neutralization process results in rapid neutralization of dithiophosphoric acid and hence neutralization promoters are not generally needed. However, in some cases it may be desirable to use such promoters in order to increase throughput. Therefore it is contemplated that the various neutralization promoters such as nitric acid, $C_1$–$C_{12}$ carboxylic acids and their salts, dialkyl dithiophosphoric acids, and the like, can be present in the neutralization mixture during the neutralization reaction.

One of the more commercially significant applications of this invention is in the manufacture of ZOP's. A process for the manufacture of zinc diaryl or dialkyl dithiophosphates comprises reacting one mole of $P_2S_5$ with about four moles of aryl or alkyl alcohol to form dithiophosphoric acid; contacting the dithiophosphoric acid with a slurry of zinc oxide in oil to form a neutralization mixture; passing said neutralization mixture through a static mixer in order to achieve mixing of the neutralization mixture and substantial neutralization of said dithiophosphoric acid; cooling the substantially neutralized dithiophosphoric acid and blowing with an inert gas to remove water of neutralization; and recovering zinc dithiophosphates.

Preferably the neutralization mixture is maintained at a temperature below 210° F to minimize decomposition.

The aryl dithiophosphates are manufactured from hydroxyl aryl compounds. These hydroxyl aryl compounds generally contain one, two or three aromatic rings but most commonly contain a single aromatic ring. Said hydroxyl aryl compounds may contain more than one hydroxy group but most commonly contain a single hydroxy group. The aromatic ring or rings may contain various other substitutions such as hydrocarbyl, chlorine, bromine, nitro and others. In some cases these substitutions do not enhance or detract from the effectiveness of the additive. In no case should the substitution interfere with the reaction with $P_2S_5$ or the neutralization step.

Commonly, hydrocarbyl substitution of the hydroxy aryl compound is desirable to order to improve the oil solubility and effectiveness of neutralized metal dithiophosphates as lubricating oil additives. Therefore, hydrocarbyl substituted hydroxy aryl compounds, such as hydrocarbyl phenols, are preferred.

The most commonly used substituted phenols contain one or more hydrocarbyl groups having about one to about 100 carbon atoms. Preferably, the hydrocarbyl groups contain about 8 to about 20 carbon atoms. The hydrocarbyl groups can be alkyl, alkenyl, aryl, aralkyl or alkaryl. Mono alkyl substitution is preferred. The hydrocarbon substitution can range from low molecular weight groups such as methyl, ethyl, propyl, isopropyl, butyl, isobutyl, and the like up to low molecular weight polymers and copolymers. Many commercially available substituted phenols contain $C_8$–$C_{20}$ substituents from polypropylene or polybutene. The hydrocarbyl substituted phenol may have other substituents, such as for example, chlorine, bromine, nitro or sulfonic acid groups.

The alkyl dithiophosphates are manufactured from hydroxy alkyl compounds such as alcohols. Metal dialkyl dithiophosphates are most commonly formed by the reaction of phosphorus pentasulfide with aliphatic alcohols to form phosphoric acid esters. The alcohols, often a mixture of alcohols, commonly contain from about 3 to about 20 carbon atoms, but preferably about 3 to about 12 carbon atoms. Sometimes dialkyl dithiophosphoric acids are represented as follows:

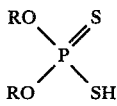

wherein R comprises an alkyl group containing about three to about twenty carbon atoms. These alkyl groups generally originate from alcohols such as propyl, n-butyl, n-pentyl, n-hexyl, n-heptyl, n-octyl, n-decyl, n-dodecyl, hexadecyl, octadecyl or branched chain alcohols such as the methyl or ethyl branched isomers of the above. Suitable branched alcohols are isopropyl, 2-methyl-1-pentanol, 2-ethyl-1-hexanol, 2,2-dimethyl-1-octanol, and alcohols prepared from olefin oligomers such as propylene dimer or trimer by hydroboration-oxidation or by the Oxo process. It may be preferable to use mixtures of alcohols because of their low cost and possible improvement in performance.

The dialkyl or diaryl dithiophosphoric acids are generally made batchwise or continuously by reaction of about 4 moles of hydroxy compound with one mole of a phosphorus pentasulfide containing about 27 weight percent phosphorus. The phosphosulfurizing agent used is phosphorus pentasulfide. The quality of the phosphorus pentasulfide is of some importance and this reagent should have approximately the following properties:
  Melting point, ° F. - - - 270–280
  Wt. percent phosphorus - - - 25–30
  Wt. percent sulfur - - - 70–75
  Free of organic material.

The diaryl or dialkyl dithiophosphoric acids are then reacted with a metal base such as zinc oxide or zinc hydroxide in order to form the metal diaryl or dialkyl dithiophosphate having a metal to phosphorus ratio of about 1–1.5:1. The neutralization reaction is usually carried out at elevated temperatures in the range of about 100° F to about 200° F. The neutralization is effected, for example, by contacting a zinc oxide slurry with diaryl dithiophosphoric acid for a time sufficient to neutralize the acid and possibly also incorporate an excess of zinc oxide so that the material is basic. The neutralization reaction may usually be completed within a period of from about 1 to about 30 minutes depending on temperature, throughput, and mixing efficiencies. Commonly, good mixing is achieved and the neutralization is substantially complete after only a few minutes, even at low space velocities through the static mixer. The neutralized product can be used as a corrosion inhibitor without the separation of oil slurrying medium or, if a highpurity zinc dihydrocarbon dithiophosphate is desired, the oil medium may be separated from the salt by solvent extraction, distillation, etc.

The oil used in the slurry is preferably a light lubricating oil; however, heavier lubricating oils can be used if desired. The lighter oils are preferred because of their lower viscosities and the greater ease of pumping such oils or slurries containing such oils. Although hydrocarbon oils and particularly petroleum oils were utilized in the procedure set out below, it is intended that other oils can also be used such as the synthetic hydrocarbon polymer oils prepared by the condensation and other methods. Ester oils are not preferred because of the possibility of their dissociation in the presence of zinc oxide under the neutralization reaction conditions. Other useable oils are the distillate fuel oils such as kerosene, heater oils, dewaxed cycle oils and the like. The light lubricating oils are particularly preferred.

One means of introducing the $P_2S_5$ into the reaction vessel is by slurrying the dry $P_2S_5$ with the alcohol or alcohols that are to be used in the process to form the dialkyl-oxy radicals of the dialkyl dithiophosphate. The slurry is preferably kept cold enough to minimize reaction of the $P_2S_5$, and alcohol prior to introduction into the reaction vessel. Sometimes it is also suitable to slurry the base, such as ZnO or $Zn(OH)_2$, in the same alcohol in order to transport it to the reactor.

The lubricating oils in which the compositions of this invention are useful as additives and which comprise a major proportion of the lubricating oil compositions may be of synthetic, animal, vegetable, or mineral origin. Ordinarily mineral lubricating oils are preferred by reason of their availability, general excellence, and low cost. For certain application, oils belonging to one of the other three groups may be preferred. For instance, synthetic polyester oils such as didodecyl adipate and di-2-ethylhexyl sebacate are often preferred as jet engine lubricants. Normally the lubricating oils preferred will be fluid oils, ranging in viscosity from about 40 Saybolt Universal seconds at 100° F to about 200 Saybolt Universal seconds at 210° F. This invention contemplates also the presence of other additives in lubricating compositions. Such additives include, for example, viscosity index improving agents, pour point depressing agents, anti-foam agents, extreme pressure agents, rust-inhibiting agents, and oxidation and corrosion inhibiting agents.

The additive combination of this invention is generally added to lubricating oil in order to improve the anitwear or antioxidant properties of said oil. Depending on the nature of the oil, the intended use and the desired improvement, different amounts of the additive are needed in order to be effective. Generally about 0.05 to about 5 weight percent, preferably from about 0.1 to about 2 weight percent, of the additive is used.

DRAWING

The attached FIGURE is a schematic diagram of a process for the manufacture of zinc dithiophosphates.

In this process $P_2S_5$ is reacted with alcohol to produce an intermediate dithiophosphoric acid, and then the dithiophosphonic is neutralized with zinc oxide to form a clear, bright yellow product. $P_2S_5$ is reacted with a mixture of $C_3$-$C_8$ alcohols. The mol ratio of alcohol to $P_2S_5$ is about 4 to 1. The alcohol 1 and the $P_2S_5$ 2 is added to a stirred tank reactor 4 for where the reaction is conducted at a temperature of about 210° to 220° F for about 30 minutes. After the reaction is complete, hydrogen sulfide formed during the reaction is stripped from the reaction mixture by blowing with nitrogen 3. The product is removed from stirred tank 4 through line 5 to heat exchanger 6 where the temperature is reduced to about 150°. Often it is desirable to filter the product dithiophosphoric acid. In this case, the product is taken through valve 26 and line 7 to filter 8 where haze and particulate matter is removed. Filter 8 is a self-cleaning Sparkler filter. The product is then transferred through line 9 and valve 27 to line 10. The product can then either be taken through valve 13 and line 12 to storage tank 15 or be passed through pump 14 to the continuous neutralization process. In another embodiment, dithiophosphoric acid which is stored in tank 13 can be supplied through line 12 and valve 13 to the continuous neutralization process. Zinc oxide 20 and unfiltered zinc dialkyl dithiophosphate product 21 is slurried in stirred vessel 23 to form a slurried zinc oxide for neutralization of the dithiophosphoric acid. The zinc oxide slurry is pumped through line 24 by metering pump 22 and injected through line 28 into line 29. The dithiophosphoric acid is pumped by centrifugal pump 14 through line 29 where it becomes combined with the zinc oxide slurry. The neutralization mixture of dithiophosphoric acid and zinc oxide is then pumped into static mixer 30 where they come into intimate contact and mixed thoroughly. Most of the neutralization reaction takes place in this static mixer in a very short period of time. Neutralization promoters can be added prior to the static mixer, however, generally none is needed. Because the neutralization reaction is highly exothermic and because it is highly desirable to maintain reaction mixture at less than 180° F, cooling is necessary. The partially, if not completely, neutralized dithiophosphoric acid leaves static mixer 30 through line 31 and passes through heat exchanger 32 to line 33 to heat exchanger 34 where substantial cooling is effected. After cooling, the partially, if not completely, neutralized dithiophosphoric acid is passed through line 35 to vessel 36. Vessel 36 is merely an enlarged portion of pipe or separate reactor which will allow extra contact time between the dithiophosphoric acid and zinc oxide. This vessel increases the probability of the reaction going to completion. In some cases, vessel 36 can be placed upstream of the static mixer, however, it is preferred to place it downstream of the mixer. The zinc dithiophosphate then travels through lines 37 and 38 to stirred reactors 39 and 40 respectively where the product is blown with nitrogen 50 in order to remove the water of neutralization. The sweetness of the product can be checked, for example, with lead acetate paper by testing samples from lines 37 and/or 38. The zinc dithiophosphate from reactors 39 and 40 then travels through lines 51 and 52 respectively either to storage 57 and 58 respectively or possibly to filtration if necessary. In the event filtration is necessary to remove haze or particulate matter, the product from line 51 is passed through valve 60 and line 64 to filter 53. Rotary vacuum filters, such as Dorr-Oliver filters are suitable for use as filters 53 and 54. Filtered product then travels through line 66 and valve 62 through line 55 to storage 57. In a like manner, zinc dithiophosphate product from line 52 passes through valve 61 and line 65 to filter 54. Filtered product from filter 54 then passes through line 67 and valve 63 to line 56 and then storage tank 58.

We claim:

1. A process for the continuous neutralization of dithiophosphoric acid with metal base comprising:
   contacting dialkyl or diaryl dithiophosphoric acid with zinc, barium, cadmium, magnesium or nickel metal base to form a neutralization mixture;
   passing said neutralization mixture through a static mixer in order to achieve mixing of the neutralization mixture and substantial neutralization of said dithiophosphoric acid;
   cooling the substantially neutralized dithiophosphoric acid; and
   recovering metal dithiophosphate.

2. The process of claim 1 wherein the metal base is zinc oxide.

3. The process of claim 1 wherein after the neutralization mixture passes through the static mixer, the mixture is passed through a vessel in order to increase the contact time between the base and the dithiophosphoric acid in the mixture.

4. The process of claim 1 wherein the neutralization mixture is blown with inert gas in order to remove water of neutralization after passing through the static mixer and essentially completely neutralized.

5. The process of claim 1 wherein about 0.5 to about 1.0 moles of metal base per mole of dithiophosphoric acid is used.

6. The process of claim 5 wherein about 0.6 to about 0.8 moles of metal base per mole of dithiophosphoric acid is used.

7. The process of claim 1 wherein the neutralization is conducted at a temperature of about 100° F to about 210° F.

8. the process of claim 1 wherein a neutralization promoter is present in the neutralization mixture during the neutralization reaction.

9. A process for the continuous neutralization of dialkyl or diaryl dithiophosphoric acid with zinc oxide comprising:
   contacting the dithiophosphoric acid with a slurry of zinc oxide in oil to form a neutralization mixture;
   passing said neutralization mixture through a static mixer in order to achieve mixing of the neutralization mixture and substantial neutralization of said dithiophosphoric acid;
   cooling the substantially neutralized dithiophosphoric acid and blowing with an inert gas to remove water of neutralization; and
   recovering zinc dithiophosphate.

10. The process of claim 9 wherein after the neutralization mixture passes through the static mixer, the mixture is passed through a vessel in order to increase the contact time between the zinc oxide and the dithiophosphoric acid in the mixture.

11. The process of claim 9 wherein about 1.3 to about 1.6 moles of zinc oxide per mole of dithiophosphoric acid is used.

12. The process of claim 9 wherein the neutralization mixture is maintained at a temperature below 210° F.

13. A process for the manufacture of zinc diaryl or dialkyl dithiophosphates which comprises:
   reacting one mole of $P_2S_5$ with about four moles of aryl or alkyl alcohol to form dithiophosphoric acid;
   contacting the dithiophosphoric acid with a slurry of zinc oxide in oil to form a neutralization mixture;
   passing said neutralization mixture through a static mixer in order to achieve mixing of the neutralization mixture and substantial neutralization of said dithiophosphoric acid;
   cooling the substantially neutralized dithiophosphoric acid and blowing with an inert gas to remove water of neutralization; and
   recovering zinc dithiophosphate.

* * * * *